United States Patent
Van Meter et al.

(10) Patent No.: US 11,951,046 B1
(45) Date of Patent: *Apr. 9, 2024

(54) RESUSCITATION CHAMBER

(71) Applicant: BAROMEDICAL RESEARCH INSTITUTE, LTD., New Orleans, LA (US)

(72) Inventors: Keith Van Meter, New Orleans, LA (US); John Engle, New Orleans, LA (US)

(73) Assignee: BAROMEDICAL RESEARCH INSTITUTE, LTD., New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,049

(22) Filed: Nov. 2, 2022

Related U.S. Application Data

(63) Continuation of application No. 17/525,304, filed on Nov. 12, 2021, now Pat. No. 11,497,668, which is a
(Continued)

(51) Int. Cl.
*A61G 10/02* (2006.01)
*A61B 1/267* (2006.01)
(Continued)

(52) U.S. Cl.
CPC .......... *A61G 10/026* (2013.01); *A61B 1/267* (2013.01); *A61B 5/022* (2013.01);
(Continued)

(58) Field of Classification Search
CPC .............. A61G 10/026; A61G 10/023; A61G 2200/325; A61G 2210/30; A61B 34/30;
(Continued)

(56) References Cited

U.S. PATENT DOCUMENTS 3,877,427 A * 4/1975 Alexeev .............. A61G 10/026
128/202.13
5,678,543 A * 10/1997 Bower .................. A62B 31/00
128/205.26
(Continued)

FOREIGN PATENT DOCUMENTS

EP         0022012 B1 * 1/1981 ........... B63C 11/325

OTHER PUBLICATIONS

English Machine Translation of EP-0022012-B1 provided by Espacenet (Year: 1981).*

*Primary Examiner* — Joseph D. Boecker
*Assistant Examiner* — Brian T Khong
(74) *Attorney, Agent, or Firm* — Garvey, Smith & Nehrbass, Patent Attorneys, L.L.C.; Seth M. Nehrbass; Fabian M. Nehrbass

(57) ABSTRACT

A resuscitation chamber apparatus for administering hyperbaric oxygen to a patient. More particularly, the present invention relates to a hyperbaric oxygen compatible critical care chamber apparatus preferably for use in emergency departments and/or prehospital ambulance management of patients. In a preferred embodiment of the present invention, the apparatus is a resuscitation monoplace hyperbaric chamber preferably used in critical care management of acutely ill or injured patients in prehospital emergency medical services (EMS) settings or in hospital emergency departments. The apparatus preferably allows a critical care shock or arrested patient to be pressurized preferably without compromise for application of best medical equipment, medications and human resuscitating intervention.

20 Claims, 4 Drawing Sheets

Related U.S. Application Data continuation of application No. 15/052,139, filed on Feb. 24, 2016, now abandoned.

(60) Provisional application No. 62/119,899, filed on Feb. 24, 2015.

(51) Int. Cl.
| | | |
|---|---|---|
| *A61B 5/022* | (2006.01) | |
| *A61B 5/145* | (2006.01) | |
| *A61B 34/30* | (2016.01) | |
| *A61H 31/00* | (2006.01) | |
| *A61M 5/142* | (2006.01) | |
| *A61M 16/04* | (2006.01) | |

(52) U.S. Cl.
CPC .......... *A61B 5/14542* (2013.01); *A61B 34/30* (2016.02); *A61H 31/004* (2013.01); *A61M 5/142* (2013.01); *A61M 16/04* (2013.01); *A61G 2200/325* (2013.01); *A61G 2210/30* (2013.01)

(58) Field of Classification Search
CPC ..... A61B 1/267; A61B 5/022; A61B 5/14542; A61B 34/35; A61H 31/004; A61M 5/142; A61M 16/04; B25J 21/02
See application file for complete search history.

(56) References Cited

U.S. PATENT DOCUMENTS

| | | | | |
|---|---|---|---|---|
| 5,685,293 | A | * 11/1997 | Watt | A61M 16/10 128/205.26 |
| 6,283,123 | B1 | * 9/2001 | Van Meter | A61G 10/026 600/323 |
| 9,474,580 | B2 | * 10/2016 | Hannaford | A61B 34/76 |
| 2002/0177117 | A1 | * 11/2002 | Wolf, Jr. | A01N 1/0247 435/284.1 |

* cited by examiner

RESUSCITATION CHAMBER

CROSS-REFERENCE TO RELATED APPLICATIONS

This is a continuation of U.S. patent application Ser. No. 17/525,304, filed 12 Nov. 2021, now U.S. Pat. No. 11,497,668, which is a continuation of U.S. patent application Ser. No. 15/052,139, filed 24 Feb. 2016, which claims priority to my U.S. Provisional Patent Application Ser. No. 62/119,899, filed 24 Feb. 2015. Priority of U.S. Provisional Patent Application Ser. No. 62/119,899, filed 24 Feb. 2015, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a resuscitation chamber apparatus for administering hyperbaric oxygen to a patient. More particularly, the present invention relates to a hyperbaric oxygen compatible critical care chamber apparatus preferably for use in emergency departments and/or prehospital ambulance management of patients. In a preferred embodiment of the present invention, the apparatus is a resuscitation monoplace hyperbaric chamber preferably used in critical care management of acutely ill or injured patients in prehospital emergency medical services (EMS) settings or in hospital emergency departments. The apparatus preferably allows a critical care shock or arrested patient to be pressurized preferably without compromise for application of best medical equipment, medications and human resuscitating intervention.

2. General Background of the Invention

The following references are incorporated herein by reference: U.S. Pat. Nos. 5,797,403; 5,865,722; 6,283,123; 6,461,290; 6,488,029; 7,469,977; 7,687,272; 7,789,820; 8,034,008; 8,181,276; and 8,549,663.

The following publications are hereby incorporated herein by reference:

Doarn et al., Evaluation of Teleoperated Surgical Robots in an Enclosed Undersea Environment., Telemedicine and e-Health. May 2009, 15(4): 325-335;

Kamler, Ken, Performing Robotic Surgery at NASA's Undersea Lab., Popular Mechanics (2009);

Müeller et al., Testing of a Modified Build-In-Breathing System for Hyperbaric Oxygen Therapy with an Online Measurement of Oxygen Consumption., http://archive.rubicon-foundation.org/6593;

Van Meter et al., Hyperbaric oxygen improves rate of return of spontaneous circulation after prolonged normothermic porcine cardiopulmonary arrest., Resuscitation. 2008 August; 78(2):200-14;

Van Meter, Keith, Hyperbaric Oxygen Therapy as an Adjunct to Pre-hospital Advanced Trauma Life Support., Surg Technol Int. 2011 Dec. 1; XXI:61-73.; and Van Meter, Keith, Hyperbaric Oxygen Clinical Application in Resuscitation from Insult of Acute Severe Anemia., Wound Care & Hyperbaric Medicine, Vol. 5 Issue 4 (2014).

BRIEF SUMMARY OF THE INVENTION

The present invention relates to a resuscitation chamber apparatus for administering hyperbaric oxygen to a hypoxic or shock patient. More particularly, the present invention relates to a hyperbaric oxygen compatible critical care chamber apparatus preferably for use in emergency departments and/or prehospital ambulance management of patients. In a preferred embodiment of the present invention, the apparatus is a resuscitation monoplace hyperbaric chamber preferably used in critical care management of acutely ill or injured patients in prehospital EMS settings or in hospital emergency departments. The apparatus preferably allows a critical care shock or arrested patient to be pressurized preferably without compromise for application of best medical equipment, medications and human resuscitating intervention.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

The present invention relates to a resuscitation chamber apparatus for administering hyperbaric oxygen to a patient. More particularly, the present invention relates to a hyperbaric oxygen compatible critical care chamber apparatus preferably for use in emergency departments and/or prehospital ambulance management of patients. In a preferred embodiment of the present invention, the apparatus is a resuscitation monoplace hyperbaric chamber preferably used in critical care management of acutely ill or injured patients in prehospital EMS settings or in hospital emergency departments. The apparatus preferably allows a critical care shock or arrested patient to be pressurized preferably without compromise for application of best medical equipment, medications and human resuscitating intervention.

In a preferred embodiment of the present invention, the apparatus is able to be used in an emergency department of a hospital and/or for patient management in an ambulance enroute to a hospital. The resuscitation monoplace hyperbaric chamber is preferably a hyperbaric chamber preferably used in critical care management of acutely ill or injured patients in prehospital EMS settings or in hospital Emergency Departments.

Figure 1:
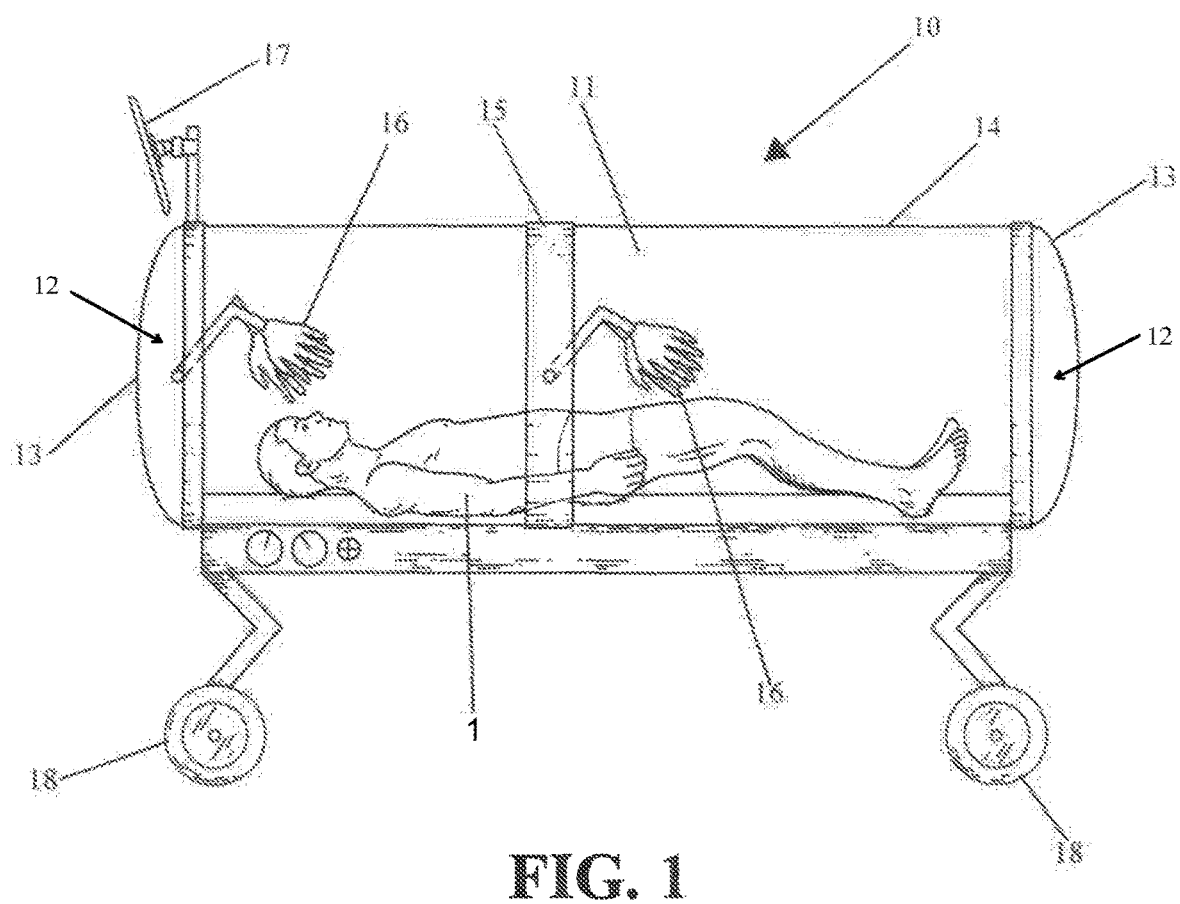
FIG. 1 shows an apparatus of a preferred embodiment of the present invention.

FIG. 1 shows an apparatus of a preferred embodiment of the present invention. As shown in FIG. 1, a patient 1 can receive treatment in the apparatus of the present invention, designated generally by the numeral 10, which comprises a hyperbaric chamber 11, opening 12, a sealing means/head 13, a tubular shell/hull 14, band 15, robotic manipulators 16, a monitor 17, and wheels 18.

In a preferred embodiment of the present invention, the apparatus comprises: a chamber sized and shaped to receive and enclose a patient comprising patient care equipment preferably disposed within the chamber, an opening, and a means to seal the opening wherein the chamber and patient are sealed from the outside environment; a means for pressurizing the chamber; a means for administering oxygen to the patient; a means for administering treatment to the patient when the chamber is sealed; and a means for monitoring the treatment administration.

The chamber is preferably sized and shaped to receive and enclose a patient, wherein the chamber preferably allows a critical care shock or arrested patient to be pressurized without compromise for application of best medical equipment, medications and human resuscitating intervention. The chamber preferably comprises a hull preferably made up of an acrylic tubular shell. Alternatively, the hull can be made up of stainless steel, acrylic plastic, or steel. The chamber also preferably comprises reinforced thick gauge stainless steel bands preferably used for reinforcement of the hull. Alternatively, the reinforcement bands can be made up of aluminum or LEXAN®.

The chamber is preferably cylindrical. Most preferably, the chamber has a diameter of 36 inches to 48 inches.

The patient care equipment preferably includes but is not limited to: mask bibs and/or endotracheal tubes to preferably overboard dump for 100% oxygen administration; a cuirass ventilator (Most preferably, a HYEK® cuirass ventilator); external cardiac chest compressor (Most preferably, a LUCAS® external cardiac chest compressor); intravenous (IV) pump that preferably penetrators through the hull while maintaining the seal of the chamber (Most preferably, a IVAC® IV pump); IO intravascular/intramedullary access (Most preferably with EASYIO®); laryngoscope (Most preferably, a GLIDESCOPE® laryngoscope); a periodic recording blood pressure cuff, or a cardiac monitor.

The sealing means of an apparatus of a preferred embodiment of the present invention is a steel head preferably sized to seal the ends of the chamber. Alternatively, the sealing means can be made up of stainless steel or aluminum.

The apparatus of a preferred embodiment of the present invention preferably includes means for pressurizing the chamber to a pressure ranging from 1.0 atmospheres to 4.0 atmospheres. More preferably, the apparatus includes means for pressurizing the chamber to a pressure ranging from 1.5 atmospheres to 4.0 atmospheres. In one embodiment of the present invention, the apparatus includes means for pressurizing the chamber to a pressure greater than 1.5 atmospheres. In an alternative embodiment, the pressurizing means can pressurize the chamber to a pressure of 3 atmospheres. In another embodiment, the pressurizing means can pressurize the chamber to a pressure of 4 atmospheres.

The pressurizing means preferably includes the step of pumping in a pressurizing gas. The pressurizing gas is preferably a nitrogen/oxygen mix. The pressurizing gas ratio of nitrogen to oxygen preferably ranges from 0% nitrogen/100% oxygen to 95% nitrogen/5% oxygen. More preferably, the pressurizing gas ratio of nitrogen to oxygen ranges from 0% nitrogen/100% oxygen to 90% nitrogen/10% oxygen. Most preferably, the pressurizing gas ratio of nitrogen to oxygen ranges from 90% nitrogen/10% oxygen to 95% nitrogen/5% oxygen. In a preferred embodiment of the present invention, the pressurizing gas is a 90%/10% nitrogen/oxygen mix.

The means for administering oxygen to the patient is preferably a closed built in overboard dump system of oxygen administration where oxygen is directly delivered to a patient via an endotracheal tube. The surface equivalent fraction of inhaled oxygen preferably ranges from 100% to 400%. Most preferably, the surface equivalent fraction of inhaled oxygen ranges from 200% to 300%. In one embodiment, the surface equivalent fraction of inhaled oxygen is 100%. In one embodiment, the surface equivalent fraction of inhaled oxygen is 190%. In one embodiment, the surface equivalent fraction of inhaled oxygen is 400%.

The means for administering treatment preferably include robotic manipulators positioned within the chamber and/or external controllers. The robotic manipulators are preferably able to control the manipulation and adjustment of patient care equipment. In a preferred embodiment of the present invention, the apparatus has a plurality of robotic manipulators and/or a plurality of external controllers. Most preferably, the apparatus has at least four robotic manipulators. The robotic manipulators and/or external controllers preferably provide hand on contact with a patient including but not limited to the following examples:

(1) administering inter-osseous routed fluids and medications;
(2) adjusting and/or applying mechanical device administered chest compression;
(3) intubating a patient's trachea to ventilate the patient by the cuirass external chest ventilator;
(4) cardiac monitoring, cardioverting, and/or defibrillating by electric shock the patient as needed;
(5) measuring via blood pressure cuff and/or intravascular manometry the blood pressure of a patient; and/or
(6) measuring a patient's transcutaneous $pO_2$ and/or blood $pO_2$ and/or measuring oximetry and tissue adenosine triphosphate (ATP) levels by polarographic soft tissue implanted needle monitor.

The means for monitoring the treatment administration is preferably a guidance flat screen monitor for the robotic arms and/or external controllers.

The apparatus of a preferred embodiment of the present invention further comprises a safety means for suppressing fire, wherein the safety means is a deluge high speed fire suppression system.

Figure 4:
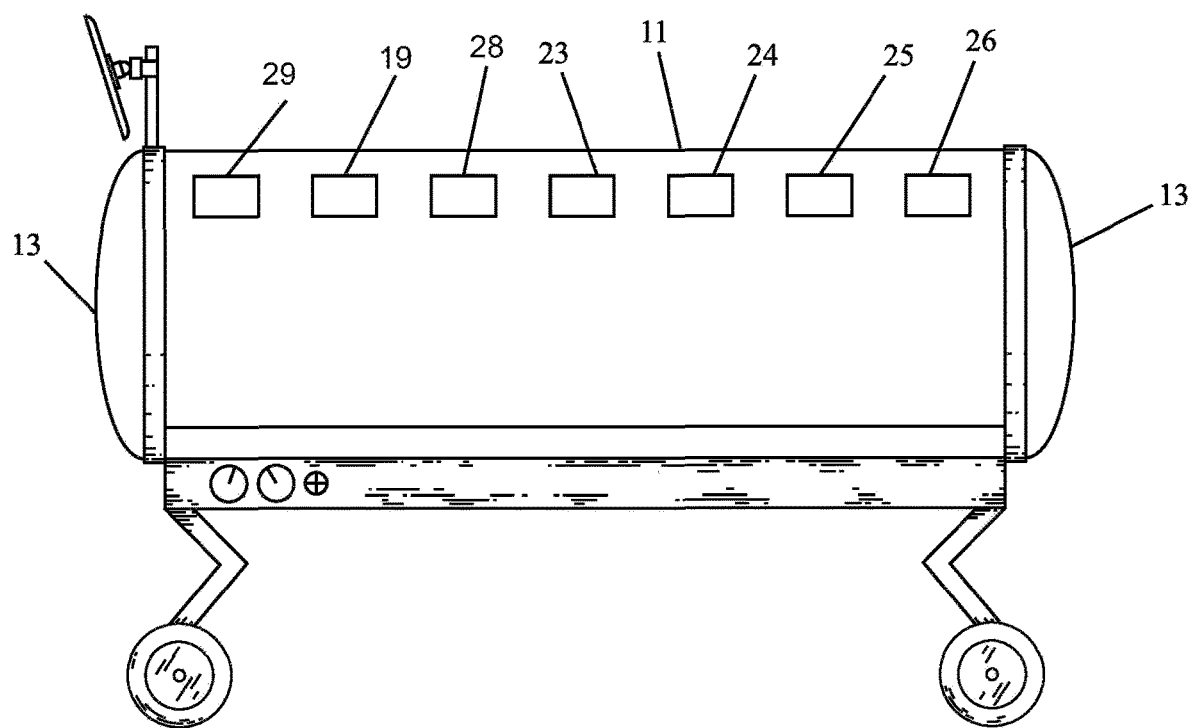
FIG. 4 shows a cutaway view of a preferred embodiment of the present invention.

In various embodiments, the apparatus allows for effect remote control of the robotic manipulators 16 (robotic arms) for manipulation through the hull and adjustment of patient care equipment. As shown in FIG. 4, the patient care equipment for adjustment of various embodiments includes: mask bibs and/or endotracheal tubes to preferably overboard dump for 100% oxygen administration; a cuirass ventilator 29 (most preferably, a HYEK® cuirass ventilator); external cardiac chest compressor 19 (most preferably, a LUCAS® external cardiac chest compressor); intravenous (IV) pump 28 that preferably penetrators through the hull while maintaining the seal of the chamber (most preferably, a IVAC® IV pump); IO intravascular/intramedullary access 23 (most preferably with EASYIO®); laryngoscope 24 (most preferably, a GLIDESCOPE® laryngoscope); a periodic recording blood pressure cuff 25; or a cardiac monitor 26.

Figure 2:
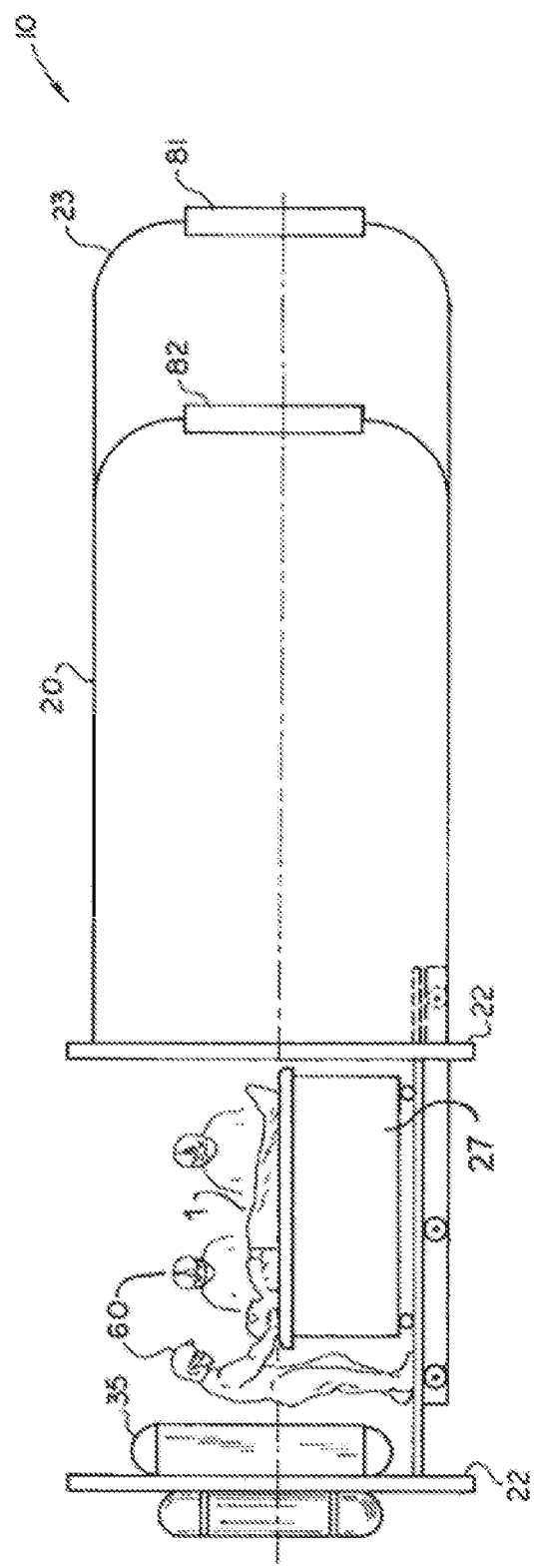
FIG. 2 shows a side view of a prior art hyperbaric resuscitation system.
Figure 3:
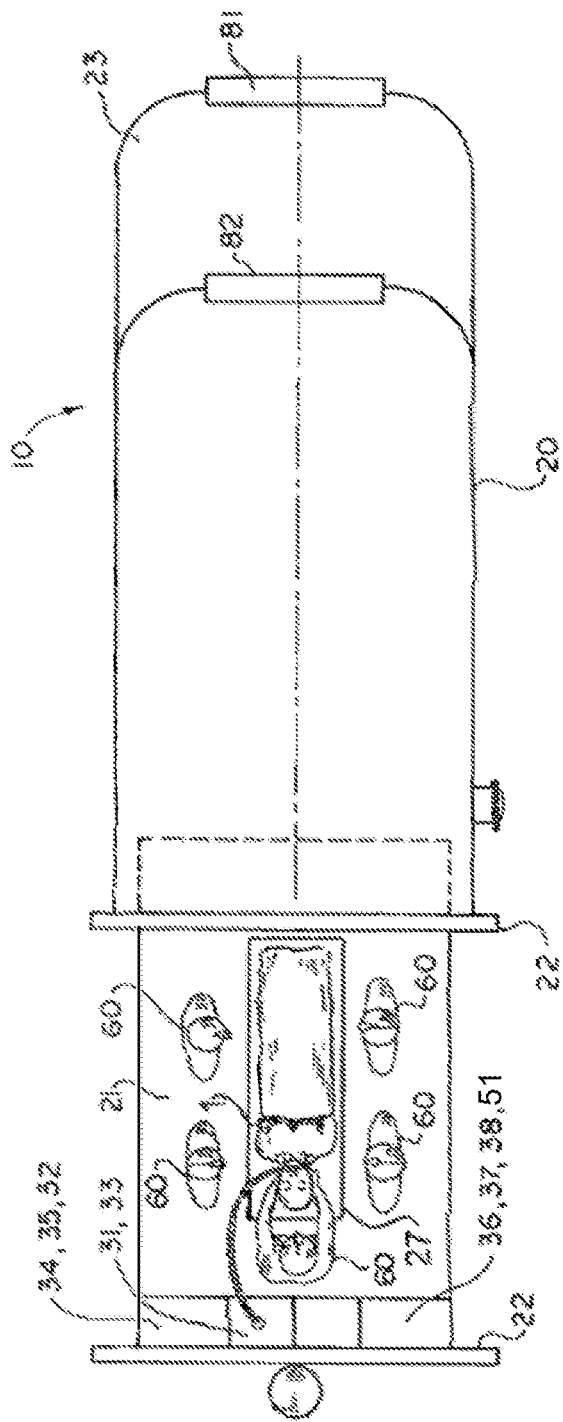
FIG. 3 shows a top view of a prior art hyperbaric resuscitation system.

FIGS. 2 and 3 show views of a prior prior art hyperbaric resuscitation system shown in FIGS. 9 and 10 and described in column 11-36 of U.S. Pat. No. 6,283,123. The system is preferably composed of a hyperbaric chamber 20 with minimum dimensions of 96" (2.44 m) in diameter with a 14' (4.27 m) usable length, capable of being pressurized to four atm abs, and built to pressure vessel human occupancy (PVHO) standards. Access to the chamber 20 can be through doors 81 and 82 large enough to roll equipment and patient 1 in and out (e.g., 34"×54"-86 cm×137 cm). Access is preferably also provided by a quick-opening closure 22 with an opening diameter equal to the diameter of the chamber 20. The entire resuscitation cart 21 will roll in and out of the chamber. The resuscitation cart comprises the patient gurney 27, floor space around the gurney 27 for two to five emergency personnel 60, a capnometer (monitor of CO2 in exhaled gas—not shown), a defibrillator/cardiac monitor 31 with intravascular pressure monitoring capability, suction equipment 32, volume cycled patient regulator/ventilator 33, American Heart Association approved code cart 34, a blood gas monitor 35, an arterial line blood pressure manometer 36, continuous EKG cardiac monitor with recorder 37, rectal core thermistor 38, x-ray equipment (not shown) for anterior/posterior neck, chest, and abdomen conventional views by portable x-my equipment, a pulse oximeter (not shown) and a NIRoscope 51 capable of rapidly and continuously measuring cytochrome oxidase redox ratio in the cerebral cortex of the patient 1.

LIST OF REFERENCE NUMERALS

The following is a list of reference numerals used in this specification:
- 1 patient
- 10 Apparatus/resuscitation monoplace hyperbaric chamber
- 11 hyperbaric chamber
- 12 Opening
- 13 Sealing means/head
- 14 tubular shell/hull
- 15 band
- 16 robotic manipulators
- 17 monitor
- 18 wheels
- 19 external cardiac chest compressor
- 20 hyperbaric chamber
- 21 resuscitation cart external cardiac chest compressor
- 22 quick-opening closure intravenous (IV) pump with through hull penetrator
- 23 IO intravascular/intramedullary access
- 24 laryngoscope
- 25 blood pressure cup/cuff with recorder
- 26 cardiac monitor
- 27 patient gurney
- 28 intravenous (IV) pump with through hull penetrator
- 29 ventilator
- 31 defibrillator/cardiac monitor
- 32 suction equipment
- 33 regulator/ventilator
- 34 code cart
- 35 blood gas monitor
- 36 arterial line blood pressure manometer
- 37 cardiac monitor with recorder
- 38 rectal core thermistor
- 51 NIRoscope
- 60 emergency personnel
- 81 door
- 82 door All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A portable hyperbaric oxygen compatible critical care chamber apparatus comprising:
   a) a chamber sized and shaped to receive and enclose a patient in a chamber interior, the chamber having one or more openings and one or more sealing heads that seal the one or more openings, the chamber, and the patient from an outside environment;
   b) said chamber pressurized to a pressure value greater than 1.5 atmospheres;
   c) a device that administers oxygen to the patient;
   d) the chamber interior having a plurality of patient care items of equipment for administering treatment to the patient when the chamber is sealed;
   e) one or more robotic arms positioned within the chamber, said one or more arms being capable of manipulating one or more of said items of equipment, wherein at least one of the one or more robotic arms is operably connected to a remote control that is external to said chamber;
   f) a means for monitoring the treatment administration; and
   g) wherein the apparatus is sized to fit within an ambulance.

2. The hyperbaric oxygen compatible critical care chamber apparatus of claim 1, wherein the chamber has a diameter of 36 to 48 inches.

3. The hyperbaric oxygen compatible critical care chamber apparatus of claim 1, further comprising a means for suppressing a fire.

4. The hyperbaric oxygen compatible critical care chamber apparatus of claim 1, wherein the one or more robotic arms are capable of contacting the patient.

5. The hyperbaric oxygen compatible critical care chamber apparatus of claim 1, wherein one or more of the one or more robotic arms is capable of interosseous administration of fluids or medications to the patient.

6. The hyperbaric oxygen compatible critical care chamber apparatus of claim 1, wherein the apparatus has one or more wheels.

7. The hyperbaric oxygen compatible critical care chamber apparatus of claim 1, wherein the equipment items include at least two of a ventilator, an external cardiac chest compressor; an intravenous pump, IO intravascular/intramedullary access, laryngoscope, blood pressure cuff, and a cardiac monitor.

8. The hyperbaric oxygen compatible critical care chamber apparatus of claim 1, wherein the apparatus is configured for use in the ambulance.

9. The hyperbaric oxygen compatible critical care chamber apparatus of claim 1, wherein the oxygen administering device includes an overboard dump system for oxygen administration.

10. The hyperbaric oxygen compatible critical care chamber apparatus of claim 9, wherein the overboard dump system for oxygen administration is capable of delivering a surface equivalent fraction of inhaled oxygen of 100% to 400% to the patient.

11. The hyperbaric oxygen compatible critical care chamber apparatus of claim 9, wherein the overboard dump system for oxygen administration is capable of delivering a surface equivalent fraction of inhaled oxygen of 190% to 400% to the patient.

12. The hyperbaric oxygen compatible critical care chamber apparatus of claim 1, wherein the chamber comprises a hull made up of stainless steel, acrylic plastic, or steel.

13. The hyperbaric oxygen compatible critical care chamber apparatus of claim 12, further comprising bands to reinforce the hull.

14. The hyperbaric oxygen compatible critical care chamber apparatus of claim 1, wherein the chamber is cylindrical.

15. A method of treating a patient with hyperbaric oxygen, comprising the steps of:
  a) providing a portable hyperbaric oxygen compatible critical care chamber apparatus with an interior that is sized and shaped to hold the patient;
  b) placing multiple patient care components in said chamber including at least two of the following components: ventilator; external cardiac compressor, intravenous pump, intravascular/intramedullary access; laryngoscope, blood pressure cuff, cardiac monitor;
  c) placing the patient in the chamber interior;
  d) maintaining a pressure in said chamber interior greater than 1.5 atmospheres;
  e) providing a robotic manipulator that is operable from a position externally of the chamber;
  f) controlling one or more of the components of step "b" with the robotic manipulator of step "e";
  g) monitoring the treatment administration via a monitor located outside the chamber; and
  h) administering a surface equivalent fraction of inhaled oxygen of 100% to 400% to the patient.

16. The method of claim 15 wherein in step "h", the surface equivalent fraction of inhaled oxygen is between 190% and 400%.

17. The method of claim 15, wherein the portable hyperbaric oxygen compatible critical care chamber apparatus has a diameter of 36 to 48 inches.

18. The method of claim 15 wherein the chamber is pressurized to a pressure of at least 3 atmospheres.

19. The method of claim 15 wherein the chamber is pressurized to a pressure of at least 4 atmospheres.

20. The method of claim 15 wherein the portable hyperbaric oxygen compatible critical care chamber apparatus comprises a means for suppressing a fire.

* * * * *